(12) United States Patent
Yang et al.

(10) Patent No.: US 11,291,811 B2
(45) Date of Patent: Apr. 5, 2022

(54) MEDICANT DELIVERY METHOD AND DEVICE THEREFOR

(71) Applicant: ZHEJIANG SANCHUANG BIOTECHNOLOGY CO., LTD., Zhejiang (CN)

(72) Inventors: Yu-Min Yang, Zhejiang (CN); Yang Yang, Zhejiang (CN)

(73) Assignee: ZHEJIANG SANCHUANG BIOTECHNOLOGY CO., LTD, Zhejiang (CN)

( * ) Notice: Subject to any disclaimer, the term of this patent is extended or adjusted under 35 U.S.C. 154(b) by 123 days.

(21) Appl. No.: 16/652,302

(22) PCT Filed: Jul. 30, 2019

(86) PCT No.: PCT/CN2019/098465
§ 371 (c)(1),
(2) Date: Mar. 30, 2020

(87) PCT Pub. No.: WO2020/024952
PCT Pub. Date: Feb. 6, 2020

(65) Prior Publication Data
US 2020/0230385 A1 Jul. 23, 2020

(30) Foreign Application Priority Data
Aug. 1, 2018 (CN) .......................... 201810867645.3

(51) Int. Cl.
*A61M 31/00* (2006.01)
*A61B 17/00* (2006.01)
(Continued)

(52) U.S. Cl.
CPC ....... *A61M 31/00* (2013.01); *A61B 17/00234* (2013.01); *A61M 39/10* (2013.01);
(Continued)

(58) Field of Classification Search
CPC ..... A61B 17/00491; A61B 2017/0042; A61M 2202/064; A61M 2210/0618; A61M 31/00; A61M 1/86; A61M 25/0136
See application file for complete search history.

(56) References Cited

U.S. PATENT DOCUMENTS 7,841,338 B2 * 11/2010 Dunne ................ A61M 15/002
128/203.12

FOREIGN PATENT DOCUMENTS

CN 203971181 U * 12/2014

* cited by examiner

*Primary Examiner* — Deanna K Hall
(74) *Attorney, Agent, or Firm* — WPAT, PC

(57) ABSTRACT

A medicant delivery method is to introduce a fluid into a container by flowing along a pressure-in pathway and out to the container. As a flow speed is stable, a connecting channel is plugged to enter the fluid to the pressure-out pathway. The fluid flows along the pressure-out pathway and then out into the container to convey the medicant at a container bottom out of the container. This method can provide more stable and more balanced forcing to gently carry the medicant all the way out of the container. Thereupon, contamination at an endoscope by the medicant bounced back from a target tissue to block vision of the endoscope can be avoided. Thus, medicant administration (hemostatic medicant for example) can be more accurate, continuity of an endoscopic surgery can be improved, performance in hemostasis can be raised, and also the total surgery time can be reduced.

7 Claims, 5 Drawing Sheets

(51) Int. Cl.
*A61M 39/10* (2006.01)
*A61M 39/22* (2006.01)
(52) U.S. Cl.
CPC ... *A61M 39/22* (2013.01); *A61B 2017/00296* (2013.01); *A61M 2202/064* (2013.01); *A61M 2210/0618* (2013.01)

MEDICANT DELIVERY METHOD AND DEVICE THEREFOR

CROSS REFERENCE TO RELATED APPLICATION

This application claims the benefits of China application Serial No. 201810867645.3, filed Aug. 1, 2018, the disclosures of which are incorporated by references herein in its entirety.

TECHNICAL FIELD

The present disclosure relates in general to a medicant delivery method, and more particularly to a method for conveying a medicant inside a container and a device for performing the method, by which the medicant can be easily transferred onto a target tissue for specific therapy.

BACKGROUND

Compounds and polymers with functions in both disease therapy and prevention can be only conveyed to patients by following specific means, such that preferable body responses can be obtained. Among all feasible means, oral administration is the most common method for conveying these compounds or polymers into a human body. In addition, other methods include injection, percutaneous absorption, pulmonary administration, nasal administration and so on. However, in order to prolong the administration interval, and also to improve patient's adaptability, a chemical coupling or embedding technique to administrate compounds or polymers is developed to enhance bioavailability of medicants, to extend the treatment within the therapeutic window, and to reduce medicant toxicity.

The compounds and the polymers can be dissolved into solvents so as to form corresponding solutions. Then, injection is applied to directly provide the solution, the pulmonary administration is applied by providing mist of the solution via a fogging device, or the percutaneous absorption is applied by mixing the solution into a wound dressing for further coating the wound. In each individual therapeutic treatment, a medicant may not be necessary. For example, in treating bleeding at the skin, tract or internal wound, direct depression upon the bleeding wound or depression further implemented by additional stitching is usually applied without using a medicant.

In addition, though a hemostatic gel may improve bleeding at the wound, yet it might be less helpful in treating a major bleeding wound in a shorter time. It is obvious that the application of the hemostatic gel has a shortcoming in timing hemostasis.

In the marketplace, a spraying product can be applied to transfer the medicant onto the wound. Such a spraying product for evenly distributing the medicant powder is actually a powder-spraying means, not a direct hemostasis device. For example, though the well-known Yun-Nan white medicinal powder spray mainly for muscle sprains can be used to treat bruises and cuts, yet, according to the instructions, some other hemostatic medicants or direct depression shall be still applied for promoting the hemostasis.

In China utility patent No. ZL201420372934.3, a hemostasis device for wound and an assembly thereof are disclosed to include a container for holding a hemostatic medicant, a valve connected with a foreign pressure source and used for controlling open/close of the container, an application tube having one bent end, and a Tee connector connecting spatially the container, the valve and the application tube. The device can perform rapid hemostasis upon a bleeding tissue. However, since a pressure overshoot exists at the moment of opening the valve to escalate the injection pressure for driving the hemostatic medicant powder, the initial injection of the hemostatic medicant powder would impact the tissue, and part of the powder would be bounced back possibly to block the field of vision upon the wound. Thereupon, continuous observation would be unfeasible. By have a laparoscopic surgery for example, the bounced-back hemostatic medicant powder would contaminate the laparoscope, and thus a clear observation for the surgery would be impossible. In other words, with this device, hemostasis effect and real-time observation of the surgery would be adversely affected, and thus the success rate and persistence of the endoscopic surgery would be reduced.

SUMMARY

An object of the present disclosure is to provide a medicant delivery method that introduces a more stable pressurized fluid source with a continuous and balanced pressure to convey the medicant.

Another object of this present disclosure is to provide a medicant delivery method that adopts a pressurized fluid to convey the medicant in a more controllable manner so as to prevent the medicant from an impulsive fluid force and thus able to push the medicant forward continuously and steadily.

A further object of this present disclosure is to provide a medicant delivery method that transmits powder medicant in a continuous and steady manner.

One more object of this present disclosure is to provide a medicant delivery device that applies a pressure source to convey a medicant to a target tissue so as to have the medicant to heal the target tissue.

One more further object of this present disclosure is to provide a medicant delivery device that a steady pressure can be applied to a medicant inside the device so as to prevent the target tissue from being impacted by the medicant.

One more further object of this present disclosure is to provide a medicant delivery device that applies a pressure source to convey a hemostatic medicant accurately to a bleeding tissue, so that repeated administrations are not necessary to perform hemostasis upon a bleeding tissue, and thus the bleeding tissue can be healed by a minimum amount of hemostatic medicant.

One more further object of this present disclosure is to provide a medicant delivery device that can prevent a target tissue from being impacted by an impulsive medicant, or from being clearly observed due to mist contamination within the field of vision (for example, powder contamination on front lens of the laparoscopy).

In this disclosure, a medicant delivery method is to introduce a fluid into a pressure-in pathway of a pressure route at a container containing thereinside a medicant. A first connecting channel is plugged to allow the fluid to enter a pressure-out pathway of the pressure route as a flow rate of the fluid is stable. The fluid leaves the pressure-out pathway via the pressure-route outlet, and then the fluid pushes and conveys the medicant out of the container via a container outlet.

In this disclosure, another medicant delivery method is to introduce a fluid into a pressure-in pathway of a pressure route at a container containing thereinside a medicant. A first connecting channel is plugged to allow the fluid to enter a pressure-out pathway of the pressure route as a flow rate of the fluid is stable. A flow direction of the fluid is turned twice in the pressure-out pathway before the fluid leaves the pressure-out pathway via a pressure-route outlet of the pressure route. Then, the fluid pushes and conveys the medicant out of the container via a container outlet after the fluid leaves the pressure-out pathway via the pressure-route outlet.

In one embodiment of this disclosure, the medicant is powdery, and has more than 90% of powder particles with a grain size ≤100 μm; preferably ≤50 μm.

In one embodiment of this disclosure, after the fluid enters the pressure-out pathway, the flow direction is turned at least once by an angle ranging between 90°~180°. In some other embodiments, the flow direction can be turned twice, three times, four times or more.

In one embodiment of this disclosure, the container has a containing volume ranging between 10 cm³~200 cm³, preferably between 10 cm³~100 cm³, and more preferably between 30 cm³~80 cm³, such as, but not limited to, 40 cm³, 41 cm³, 42 cm³, 43 cm³, 44 cm³, 45 cm³, 46 cm³, 47 cm³, 48 cm³, 49 cm³, 50 cm³, 51 cm³, 52 cm³, 53 cm³, 54 cm³, 55 cm³, 56 cm³, 57 cm³, 58 cm³, 59 cm³, 60 cm³, 61 cm³, 62 cm³, 63 cm³, 64 cm³, 65 cm³, 66 cm³, 67 cm³, 68 cm³, 69 cm³, 70 cm³, 71 cm³, 72 cm³, 73 cm³, 74 cm³, 75 cm³, 76 cm³, 77 cm³, 78 cm³, 79 cm³ and 80 cm³.

In one embodiment of this disclosure, the flow rate of the fluid is ranging between 0.3 L/min≡7 L/min, preferably between 0.5 L/min-4 L/min. In addition, a cross-sectional action area of the fluid at the pressure-route outlet is ranging between 10 mm²~200 mm², preferably between 10 cm²~100 cm², and more preferably between 20 cm²~80 cm², such as, but not limited to, 40 cm², 41 cm², 42 cm², 43 cm², 44 cm², 45 cm², 46 cm², 47 cm², 48 cm², 49 cm², 50 cm², 51 cm², 52 cm², 53 cm², 54 cm², 55 cm², 56 cm², 57 cm², 58 cm², 59 cm², 60 cm², 61 cm², 62 cm², 63 cm², 64 cm², 65 cm², 66 cm², 67 cm², 68 cm², 69 cm², 70 cm², 71 cm², 72 cm², 73 cm², 74 cm², 75 cm², 76 cm², 77 cm², 78 cm², 79 cm² and 80 cm².

In this disclosure, a device for conveying a medicant comprises:
a container for containing the medicant;
a pressure route, including an extending pathway, a pressure-route inlet and a pressure-route outlet, the pressure-route outlet extending toward a bottom of the container; and
a valve body, disposed in the pressure route, dividing the extending pathway into a pressure-in pathway and a pressure-out pathway, the pressure-out pathway having one end thereof connected with the pressure-in pathway and another end thereof connected with the pressure-route outlet.

In one embodiment of this disclosure, the device further includes a connecting port disposed at the container, and one end of the connecting port for introducing the fluid is connected with a pressure source.

In this disclosure, another device comprises:
a container for containing a medicant;
a connecting port, disposed at the container and used for connecting a pressure source;
a pressure route, extending inside the container, including an extending pathway, a pressure-route inlet and a pressure-route outlet, the pressure-route inlet being connected with the connecting port, the pressure-route outlet being disposed by facing a bottom of the container; and
a valve body, disposed in the pressure route, dividing the extending pathway into a pressure-in pathway and a pressure-out pathway, the pressure-out pathway having one end thereof connected with the pressure-in pathway and another end thereof connected with the pressure-route outlet.

In one embodiment of this disclosure, the valve body is to change at least once the flow direction of the fluid along the pressure-out pathway. In some other embodiments, the flow direction can be turned twice, three times, four times or more.

In one embodiment of this disclosure, the valve body further includes a first turning member disposed inside the pressure-out pathway to turn the flow direction of the fluid in the pressure-out pathway for the first time.

In one embodiment of this disclosure, the valve body further includes a second turning member disposed inside the pressure-out pathway to turn the flow direction of the fluid in the pressure-out pathway for the second time.

In one embodiment of this disclosure, after the valve body turns at least twice the flow direction of the fluid in the pressure-out pathway, the fluid in the pressure-out pathway flows toward the pressure-route outlet.

In one embodiment of this disclosure, the pressure source is to provide a pressurized fluid such as a gas or a liquid, preferably a gas such as, but not limited to, air, $N_2$, $O_2$, $CO_2$ or an inert gas.

In one embodiment of this disclosure, another device further includes a medicant contained inside the container, and the medicant is powdery and has more than 90% of powder particles with a grain size 100 μm; preferably ≤50 μm.

In this disclosure, the medicant enters the container via the pressure-route outlet, and leaves the container via a container outlet.

In order to apply the medicant directly onto a target tissue, a connection tube is further furnished to the container outlet. The connection tube may have an inner diameter of 2.2 mm, for example, to engage the medicant delivery device of this disclosure. Through the connection tube to guide the conveying path of the medicant, and also to have the medicant to be discharged at a place approaching the target tissue, the connection tube may have a length ranging between 13 cm-45 cm. To different target tissue, the connection tube might be varied accordingly. For example, for a nasal tissue, the connection tube shall have a length of 13 cm; and, for an intrapelitoneal tissue, the length of the connection tube can be adjusted to a length about 38 cm. In this disclosure, the medicant delivery device may be manufactured as a unique piece by die casting or 3-D printing.

In this disclosure, a medicant delivery apparatus includes a medicant delivery device and a connection tube.

In order to facilitate the endoscopic surgery, and to avoid the adverse impact or reactive bounce back of the medicant upon the target tissue so as to block the field of vision of the endoscope by contaminating the medicant powder, this disclosure further provide a pressure-adjusting assembly to engage the medicant delivery device. The pressure-adjusting assembly, the connection tube and the device of this disclosure can be manufactured as a unique piece by die casting or 3-D printing.

In this disclosure, another medicant delivery apparatus includes a medicant delivery device, a connection tube and a pressure-adjusting assembly.

In this disclosure, a pressure-adjusting assembly includes:
a pressure-adjusting tunnel has one open end connected with the connection tube, and another open end of the pressure-adjusting assembly has a tunnel wall forming an angle, ranging between 3°~10°, with an axial direction of the pressure-adjusting tunnel.

The medicant is discharged directly onto a target tissue via another open end of the connection tube.

In order to improve the pressure applied on the target tissue, another pressure-adjusting assembly of this disclosure includes:

a pressure-adjusting tunnel, having a tunnel inlet connected with the connection tube and a tunnel outlet further having a tunnel wall forming an angle with an axial direction of the pressure-adjusting tunnel, in which the angle is ranging between 10°~12.5°;

an injection nozzle, having an injection-nozzle inlet engaged with the tunnel outlet and an injection-nozzle outlet further having a tunnel wall forming an angle with an axial direction of the injection nozzle, in which the angle is ranging between 5°~6°; and in a radial direction of the pressure-adjusting tunnel, the tunnel wall of the pressure-adjusting tunnel further including a plurality of grooves.

The injection-nozzle inlet and the tunnel outlet have the same diameter, and a buffer segment is disposed between the injection-nozzle inlet and the injection-nozzle outlet. The buffer segment has an axial length of 0.5 mm~2 mm, preferably 0.5 mm~1.5 mm.

The medicant is discharged directly onto the target tissue from an open end of the pressure-adjusting assembly.

In this disclosure, various devices can be applied to pair the connection tube and the pressure-adjusting assembly by assembling, 3D printing or die casting. The device, the connection tube and the pressure-adjusting assembly can be manufactured as a unique piece for transferring the medicant. In applications, for these products to be all disposable medical supplies, manufacturing and use would be much easier.

Advantages of this Disclosure

The method of this disclosure can provide more stable and more balanced forcing to convey accurately and smoothly the medicant inside the container to the bleeding tissue, such that multiple hemostatic operations upon the bleeding tissue can be avoided, and also that only a proper amount of hemostatic medicant is needed for hemostasis at the bleeding tissue.

The method of this disclosure can provide more stable and more balanced forcing to output more gently the medicant from the container, such that bounce back effect of the medicant with respect to the target tissue would be prevented from blocking the field of vision of the endoscope, and so the continuity of the endoscopic surgery can be improved.

The method of this disclosure can concentrate the distribution of the medicant over the target tissue, especially the bleeding tissue, so that the administration of the hemostatic medicant can be more accurate. For example, more than 75% of the medicant can be limited within an area having a radius between 0.5 cm~1.5 cm.

The method of this disclosure can concentrate the medicant propelled by the pressure source over the target tissue, especially the bleeding tissue, such that more medicant can be directly applied to the bleeding wound surface, and so the hemostasis time can be significantly shortened; for example, effective hemostasis within 20 seconds.

The device of this disclosure, after connected with a pressure source, can provide more stable and more balanced forcing to propel gently the medicant inside the container, such that bounce back effect of the medicant with respect to the target tissue can be reduced so as not to block the field of vision of the endoscope, then the treatment on the target tissue (in particular, the hemostatic treatment) can be clearly observed, and so the continuity of the endoscopic surgery can be improved.

The device of this disclosure, after engaging the pressure-adjusting assembly, can have the medicant driven by the pressurized fluid more concentrated on the target tissue. In particular, to a bleeding tissue, the coverage of the hemostatic medicant can be better controlled to limit more than 75% of the medicant within an area having a radius ranging between 0.5 cm~1.5 cm.

The device of this disclosure can concentrate the medicant propelled by the fluid from the pressure source on the target tissue. In particular, to a bleeding tissue, more medicant can act directly on the bleeding wound surface, so that the medicant can effectively reach a hemostasis state in 20 seconds, for example. Thus, with the hemostasis time able to be significantly reduced, the amount of the hemostatic medicant for healing the bleeding tissue can be better controlled.

In comparison with the solutions provided by China Utility Patent No. ZL201420372934.3, the device provided by this disclosure can convey the hemostatic medicant powder directly and accurately to the bleeding tissue, such that the bounce back effect of the hemostatic medicant powder can be avoided. Thereupon, possible powder contamination to make vague the field of vision of the endoscope would be inhibited, and thus the endoscopic surgery can be normally operated. Also, since the hemostatic treatment can be directly and accurately performed on the bleeding tissue, the total time for the endoscopic surgery can be greatly reduced.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

Figure 1:
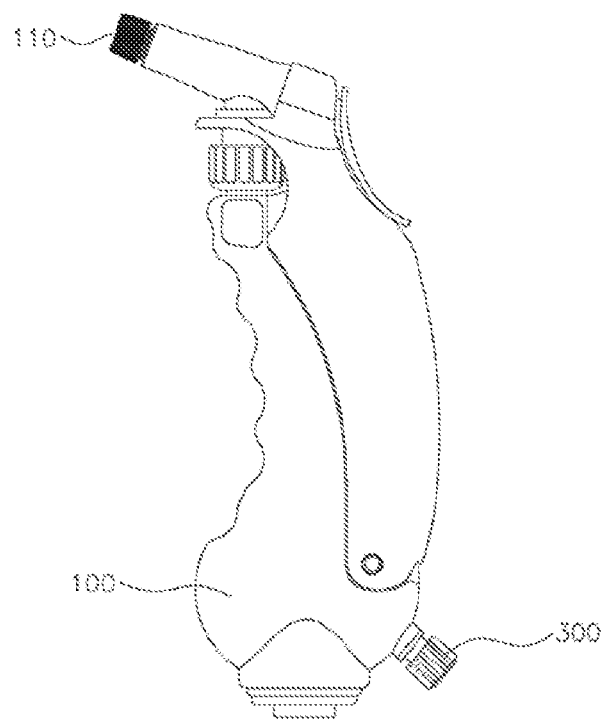
FIG. 1 is a schematic view of an embodiment of a device for performing a method in accordance with this disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
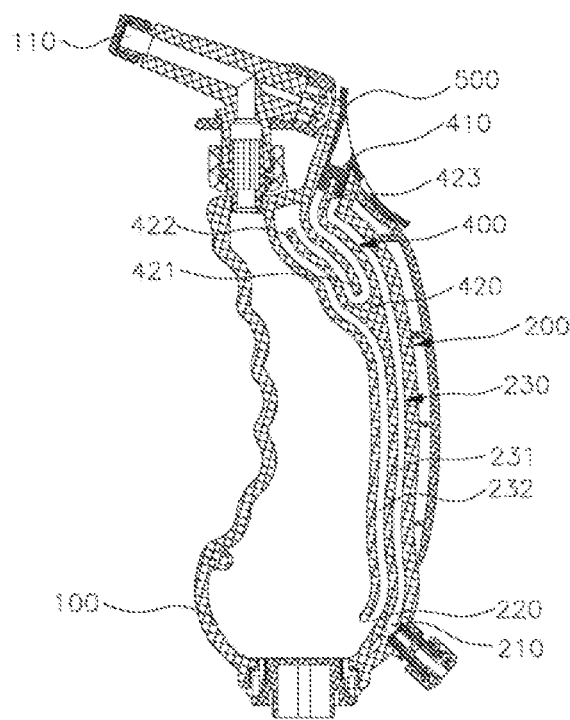
FIG. 2 is a schematic cross-sectional view of FIG. 1.

Refer now to FIG. 1 and FIG. 2; where FIG. 1 is a schematic view of an embodiment of a device for performing a method in accordance with this disclosure, and FIG. 2 is a schematic cross-sectional view of FIG. 1. As shown, in this embodiment, the device includes a container 100 and a pressure route 200. A connecting port 300, furnished to the container 100, is used for connecting a pressure source. In this embodiment, the pressure source provides an expected pressurized fluid, either a gas or a liquid, preferably a gas such as, but not limited to, air, $N_2$, $O_2$, $CO_2$ or an inert gas. The connecting port 300 is further connected with the pressure route 200 so as to introduce the pressurized fluid into the pressure route 200.

The pressure route 200, furnished inside the container 100, includes an extending pathway 230, a pressure-route inlet 210 and a pressure-route outlet 220. The pressure-route inlet 210 is connected with the connecting port 300, and the pressure-route outlet 220 is disposed to face a bottom of the container 100. The pressurized fluid is introduced into the extending pathway 230 via the pressure-route inlet 210, so as to flow along the extending pathway 230. The pressurized fluid leaves the extending pathway 230 via the pressure-route outlet 220, and then meets the medicant inside the container 100. The medicant, then driven by the pressurized fluid, is conveyed therewith and toward a container outlet 110.

Figure 7:
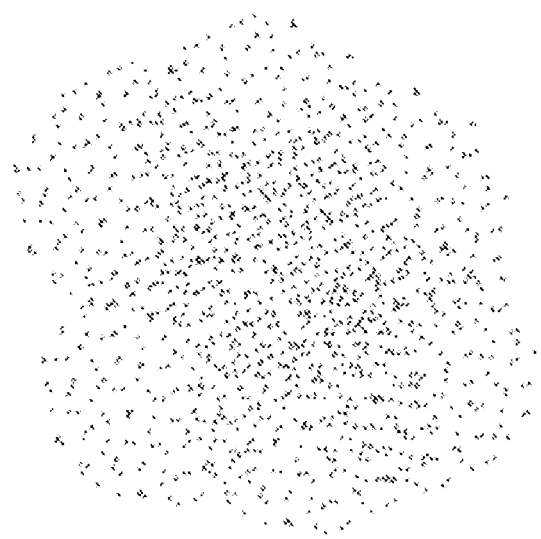
FIG. 7 is a schematic view of a medicant distribution on a target tissue by a conventional design.

After a pressure-source valve is opened, the fluid from the pressure source would enter the pressure route 200, and then flow quickly to leave the pressure route 200 via the pressure-route outlet 220, such that the medicant close to the pressure-route outlet 220 would be suddenly driven to move toward the container outlet 110. After the medicant with a larger momentum hits a target tissue, a reaction from the target tissue would broaden an area to accept the medicant as shown in FIG. 7. Accordingly, the medicant is dispersedly distributed, and thus the concentration of the medicant on the target tissue is reduced as well. Hence, while in an endoscopic surgery, with the reaction from the target tissue, the medicant would scatter all over the field of vision, by which a normal endoscopic surgery would be hard to proceed. Thus, it is inevitable to suspend the surgery, and to retrieve the endoscope for cleaning. Thereupon, continuity and efficiency of the endoscopic surgery would be affected.

In order to avoid the aforesaid situation, the device of this disclosure further includes a valve 400, and the valve 400 includes a first connecting channel 410 and a valve body 420. The first connecting channel 410, open to the atmosphere, is connected individually and spatially far to the pressure-route inlet 210 and the pressure-route outlet 220. The valve body 420, disposed inside the pressure route 200, would separate the extending pathway 230 into a pressure-in pathway 231 and a pressure-out pathway 232.

After the pressure-source valve is opened, the fluid from the pressure source would pass through the pressure-route inlet 210 and then enter the pressure route 200 to flow along the pressure-in pathway 231 before entering the first connecting channel 410. Upon when the fluid flow from the pressure source is stable, an optional blocking member 500 applied to plug the first connecting channel 410 can allow the fluid from the pressure source to enter the pressure-out pathway 232 and then to leave via the pressure-route outlet 220 to meet the medicant at the bottom of the container 100. According to this disclosure, the fluid from the pressure source can be present to drive the medicant in a more stable manner by controlling the blocking member 500 to plug or open the first connecting channel 410. In the case that the first connecting channel 410 is plugged, then the pressured fluid would flow from the pressure-in pathway 231 to the pressure-out pathway 232. On the other hand, in the case that the first connecting channel 410 is open, then the pressured fluid from the pressure-in pathway 231 would be directly discharged into the atmosphere. Since forcing upon the medicant can be more evenly, thus, when the medicant hits the target tissue, the reaction from the target tissue would be reduced, and the medicant would be more concentrated on the target tissue.

To an endoscopic surgery, the device reduces the reaction of the target tissue against the medicant, so that the medicant would not be severely bounced back to contaminate the endoscope by partly blocking the field of vision, and such that the surgery can be continuously executed. Timing for plugging the first connecting channel 410 can be determined according to practical situations. For example, in a surgery, a user can use his/her thumb to depress the blocking member 500 to plug the first connecting channel 410. While the first connecting channel 410 is plugged, the fluid from the pressure source would be led into the pressure-out pathway 232, and then leave the pressure route 200 via the pressure-route outlet 220. Obviously, the operation of the device is much easier that the prior art. For another example, in a product package, with the blocking member 500 to plug the first connecting channel 410, insides of the device can be kept sterile during transportation and storage.

In order to control the flow rate of the fluid from the pressure source, a flowmeter can be used for monitoring and facilitating the adjustment of the flow rate.

In order to prevent the fluid from the pressure source in an initial stage of entering the extending pathway 230 from hitting the medicant with an overshoot momentum, the valve body 420 can further include a guide member 423 for guiding the pressure-in pathway 231 and the pressure-out pathway 232 to extend toward the first connecting channel 410.

Empirically, by changing a flow direction of the fluid from the pressure source, the aforesaid problem in overshoot momentum upon the medicant at the early stage while the fluid entering the extending pathway 230 can be substantially resolved so as to have the forcing upon the medicant in a more stable and smoother manner. In the device of this disclosure, a commutator can be furnished to the valve body 420 so as to turn the flow direction of the fluid in the pressure-out pathway 232 at least once by 90°~180°. In some other embodiments, the flow direction can be turned twice, three times, four times or more times.

In this embodiment, the valve body 420 further includes a first turning member 421 disposed in the pressure-out pathway 232 for making the first 180° turn of the fluid in the pressure-out pathway 232. In addition, a second turning member 422 can be also included in the pressure-out pathway 232, such that the pressure-out pathway 232 can make its second 180° turn before flowing toward the pressure-route outlet 220. In the case that the grain size of the medicant is too small, more commutators can be applied to change the flow direction of the fluid, such that the forcing upon the medicant by the fluid can be much gentle. Thereupon, the aforesaid problems in overshoot momentum, excessive reaction from the target tissue, broader medicant action area (as shown in FIG. 7), disperse medicant distribution, and less medicant concentration on the target tissue.

In this disclosure, the medicant for the target tissue is powdery with more than 90% of the particles having a grain size ≤100 μm, preferably ≤50 μm. The fluid discharged from the pressure-route outlet 220 would push the medicant to move toward the container outlet 110 so as to allow the medicant to coat the target tissue.

In order to have the medicant to be directly applied to the target tissue, a connection tube 600 can be furnished to the container outlet 110 of the device. The connection tube 600 is used for guiding the medicant leaving the container outlet 110, so that the medicant can be discharged in a position close to the target tissue.

In order to help the endoscopic surgery, to avoid possible impact at the target tissue by the medicant, and to lessen the contamination of the endoscope by the bounce-back medicant, this disclosure further provides a pressure-adjusting assembly 700 to cooperate the device and the connection tube 600.

Figure 3:
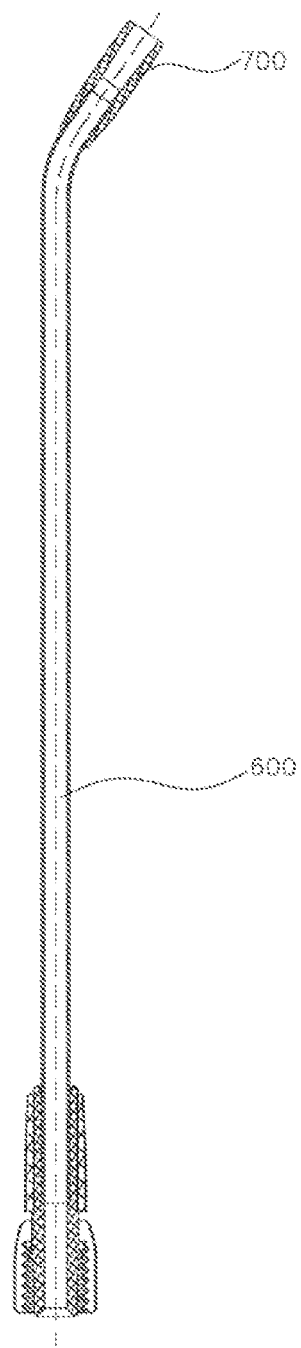
FIG. 3 is a schematic cross-sectional view of an embodiment of the connection tube furnished with a pressure-adjusting assembly in accordance with this disclosure.
Figure 5:
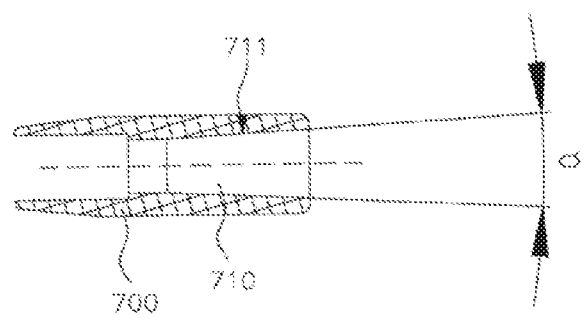
FIG. 5 is a schematic cross-sectional view of an embodiment of the pressure-adjusting assembly in accordance with this disclosure.
Figure 8:
FIG. 8 is a schematic view of a medicant distribution on a target tissue by the apparatus of this disclosure.

FIG. 3 is a schematic cross-sectional view of an embodiment of the connection tube furnished with a pressure-adjusting assembly 700 in accordance with this disclosure, and FIG. 5 is a schematic cross-sectional view of an embodiment of the pressure-adjusting assembly in accordance with this disclosure. As shown, in this embodiment, the pressure-adjusting assembly 700 includes a pressure-adjusting tunnel 710 having an open end connected with the connection tube 600 and another open end having a tunnel wall 711 forming an axial angle with the pressure-adjusting tunnel by 3°~10°. The medicant guided by the connection tube 600 would be discharged via the pen end having the 3°~10° axial angle, and then applied onto the target tissue by forming an action area shown in FIG. 8.

Figure 6:
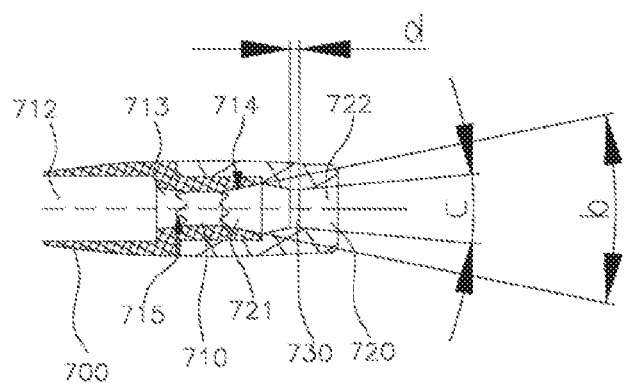
FIG. 6 is a schematic cross-sectional view of another embodiment of the pressure-adjusting assembly in accordance with this disclosure.

FIG. 6 is a schematic cross-sectional view of another embodiment of the pressure-adjusting assembly in accordance with this disclosure. As shown, the pressure-adjusting assembly 700 includes a pressure-adjusting tunnel 710 having a tunnel inlet 712 connected with the connection tube 600 and an opposing tunnel outlet 713 having a tunnel wall 714 forming an axial angle b with the pressure-adjusting tunnel 710 by 10°~12.5°. In addition, along a radial direction of the pressure-adjusting tunnel 710, a plurality of grooves 715 is furnished to the tunnel wall of the pressure-adjusting tunnel 710.

Figure 9:
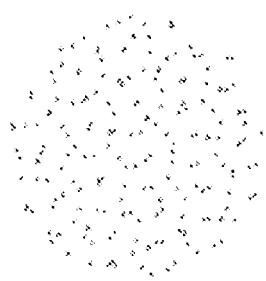
FIG. 9 is a schematic view of another medicant distribution on a target tissue by the apparatus of this disclosure.

Also, an injection nozzle 720 is furnished to a front portion of the pressure-adjusting tunnel 710. The injection nozzle 720 has an injection-nozzle inlet 721 connected with the tunnel outlet 713 and an injection-nozzle outlet 722 having a tunnel wall forming an axial angle c with the injection nozzle 720 by 5°~6°. With the connection tube 600 to discharge the medicant from the open end having the axial angle, the medicant can be directly applied to the target tissue by forming a medicant action area on the target tissue, as shown in FIG. 9.

In this embodiment, the injection-nozzle inlet 721 and the tunnel outlet 713 have the same diameter. Between the injection-nozzle inlet 721 and the injection-nozzle outlet 713, a buffer segment 730 is formed by having an axial length d of 0.5 mm~2 mm, preferably 0.5 mm~1.5 mm.

Figure 4:
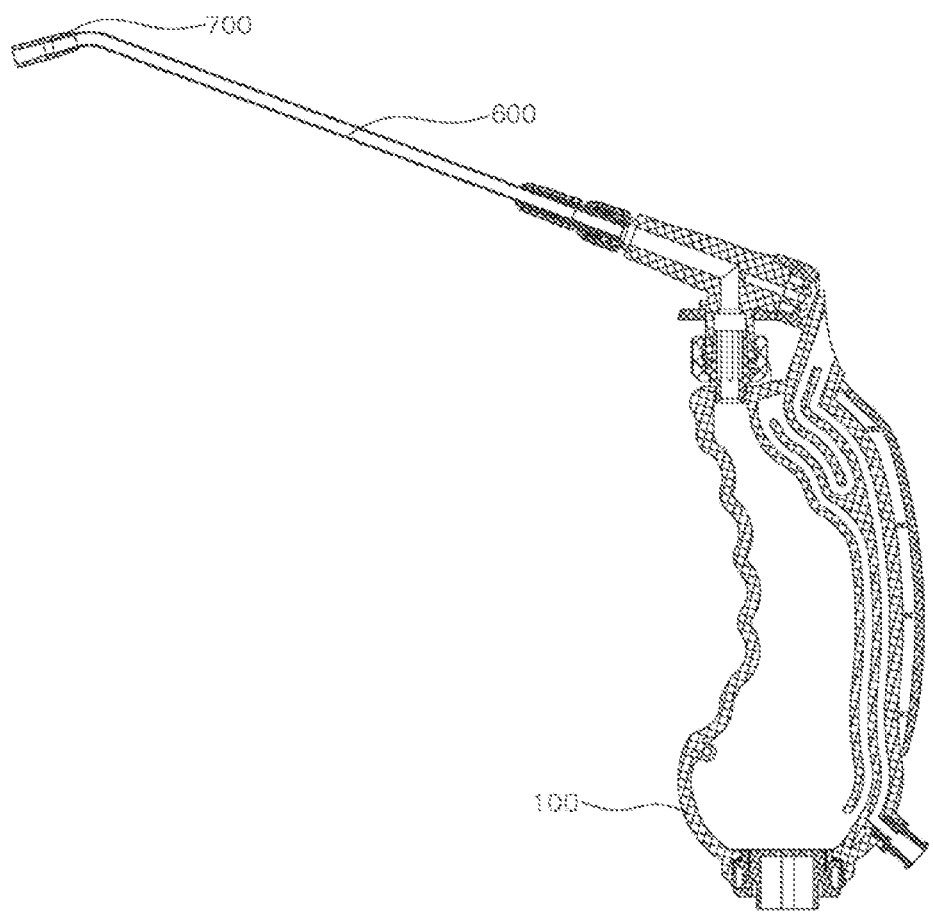
FIG. 4 is a schematic cross-sectional view of an embodiment of the apparatus in accordance with this disclosure.

FIG. 4 is a schematic cross-sectional view of an embodiment of the apparatus in accordance with this disclosure. Referring to FIG. 1 and FIG. 4, the apparatus of this disclosure is further furnished with a pressure-adjusting assembly 700 disposed at one end of the connection tube 600, while another end of the connection tube 600 is connected with the device. With the hemostatic medicant (see ZL2015100443818) loaded to the apparatus of this disclosure for performing hemostasis treatment upon a bleeding tissue, the connecting port 300 and the air source are connected to introduce a pressurized fluid. Then, the connection tube 600 is moved to aim at the bleeding target tissue, and then the blocking member 500 at the first connecting channel 410 is depressed so as to allow the pressurized fluid to enter the pressure-out pathway 232. After two 180° turns, the fluid would move toward the pressure-route outlet 220, and meet the medicant after being discharged into the container 100 via the pressure-route outlet 220. With the flow of the fluid, the medicant at the bottom of the container 100 would be driven to be discharged via the free open end of the connection tube, and then applied to the bleeding wound surface. By adjusting the flow rate of the fluid, the hemostasis process at the target tissue can be preferably observed.

Figure 10:
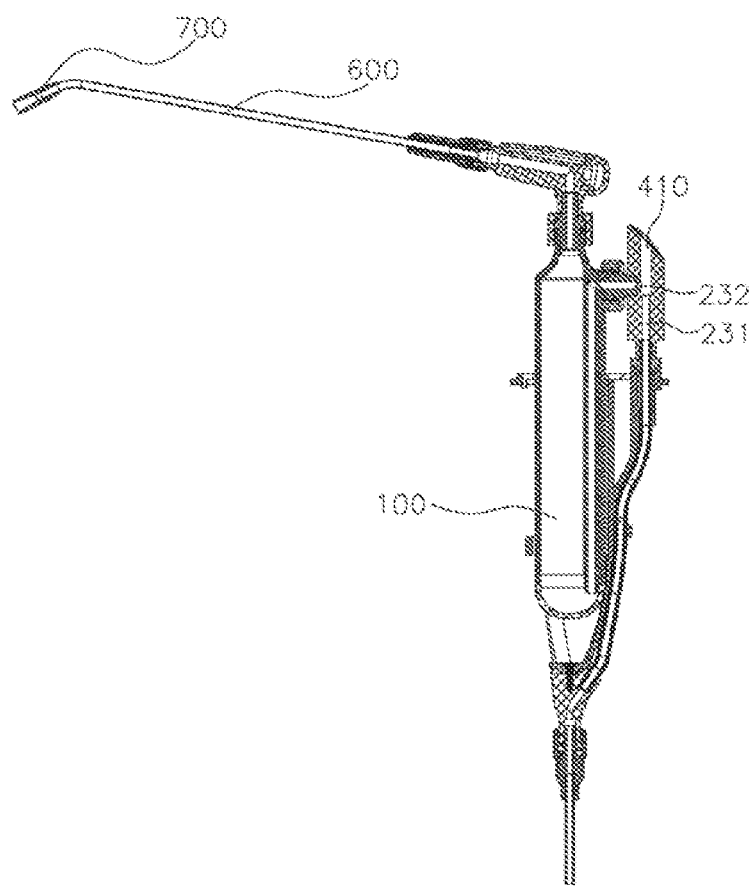
FIG. 10 is a schematic cross-sectional view of another embodiment of the apparatus in accordance with this disclosure.

FIG. 10 is a schematic cross-sectional view of another embodiment of the apparatus in accordance with this disclosure. As shown, the pressure-adjusting assembly 700 (FIG. 6) of this apparatus is assembled to one end of the connection tube 600, while another end of the connection tube 600 is connected with the device. The container 100 of the device has a containing volume of 15 cm³. The pressurized fluid is firstly introduced into the pressure-in pathway 231. As the flow of the fluid is stable, the first connecting channel 410 is plugged so as to allow the pressurized fluid into the pressure-out pathway 232. After experiencing one 90° turn, the fluid would flow downward toward the pressure-route outlet 220, and would meet the medicant out of the pressure-route outlet 220. With the momentum of the fluid, the medicant at the bottom of the container 100 would be driven to the connection tube 600. The medicant would finally be discharged out of the apparatus via the free open end of the connection tube 600 to be further applied to the bleeding wound surface by forming a medicant action area on the target tissue as shown in FIG. 9.

The method and the device provided by this disclosure can provide stable and balanced forcing to gently carry the medicant inside the container, such that the field of vision of the endoscope can be prevented from contamination of the medicant bounced back by the target tissue, in a manner of blocking the field of vision or attaching the surface of the endoscope, either of which would lead to observation difficulty of the endoscope at the target tissue (especially for the hemostasis stage of the target tissue under the hemostatic treatment), Thereupon, operational continuity of the endoscopic surgery can be significantly improved.

A middle lobe of Rat's liver is cut to make a large-scale bleeding. In the reference, a hemostatic gauze is applied directly by depression to stop the bleeding. However, bleeding still exists to all animals except for one. Among these bleeding reference, the bleeding loss is significant, and the bleeding time is comparative long. On the other hand, with the device of this disclosure to apply the hemostatic medicant to the target middle lobe, the bleeding loss at the lever is greatly reduced. In comparison with the reference, the difference between the groups is huge (p<0.001). The comparisons at the bleeding loss and the bleeding time for these two groups are listed in Table 1 as follow. It is shown that the comparison demonstrates significant difference (p<0.01) between the reference and the device of this disclosure.

TABLE 1

| Groups | Animal number (n) | Bleeding loss (g) | Bleeding time (s) |
|---|---|---|---|
| Reference | 10 | 0.64 ± 0.29 | 151.20 ± 47.73 |
| Device of Disclosure | 10 | 0.15 ± 0.07*** | 107.00 ± 31.24** |

Note:
in comparison with the reference, "*" stands for p < 0.05, and "***" stands for p < 0.001

In this test, rat's femoral artery is cut to make serious bleeding. In the reference, a hemostatic gauze is applied directly by depression to stop the bleeding. However, the bleeding loss is still significant. In the reference, 3 animals demonstrate total failure in hemostasis, and the rest show incomplete hemostasis. In all reference animals, the bleeding time is relative long. However, with the device of this disclosure to apply the hemostatic medicant, the bleeding loss is dropped (p<0.05), and the bleeding time is remarkably decreased. In statistics, these two groups demonstrate significant difference (p<0.001). In this test, no animal can reach a complete hemostasis. These results are listed in Table 2.

TABLE 2

| Groups | Animal number (n) | Bleeding loss (g) | Bleeding time (s) |
|---|---|---|---|
| Reference | 10 | 0.96 ± 0.40 | 252.9 ± 42.42 |
| Device of Disclosure | 10 | 0.59 ± 0.23* | 145.5 ± 43.02*** |

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A device, characterized in that the device comprises:
   A container, used for containing a medicant;
   A pressure route, including an extending pathway, a pressure-route inlet and a pressure-route outlet, the pressure-route outlet extending toward a bottom of the container;
   A valve body, disposed in the pressure route, dividing the extending pathway into a pressure-in pathway and a pressure-out pathway, the pressure-out pathway having one end thereof connected with the pressure-in pathway and another end thereof connected with the pressure-route outlet; and
   a fluid, pressurized to flow in the pressure route, being one of a gas and a liquid.

2. The device of claim 1, characterized in that the device further includes a connecting port disposed at the container, one end of the connecting port being connected with a pressure source while another end thereof is connected with the pressure inlet.

3. The device of claim 1, characterized in that, after the valve body turns twice a flow direction of the fluid in the pressure-out pathway, the fluid inside the pressure-out pathway is turned to flow toward the pressure-route outlet.

4. The device of claim 1, characterized in that the medicant is powdery, and has more than 90% of powder particles having a grain size ≤100 μm.

5. An apparatus, characterized in that the apparatus comprises the device of claim 1, a connection tube and a pressure-adjusting assembly, the pressure-adjusting assembly includes a pressure-adjusting tunnel, the pressure-adjusting tunnel has a tunnel inlet connected with the connection tube and a tunnel outlet having a tunnel wall forming an axial angle with the pressure-adjusting tunnel, and the axial angle is ranging between 10°~12.5°.

6. The apparatus of claim 5, characterized in that the tunnel wall of the pressure-adjusting tunnel is furnished with a plurality of radial grooves.

7. The apparatus of claim 5, characterized in that the pressure-adjusting assembly further includes an injection nozzle, the injection nozzle has an injection-nozzle inlet assembled with the tunnel outlet, an injection-nozzle outlet, and a buffer segment disposed between the injection-nozzle inlet and the injection-nozzle outlet, the buffer segment having an axial length raging between 0.5 mm~2 mm.

* * * * *